United States Patent [19]

Lindley et al.

[11] Patent Number: 4,572,916

[45] Date of Patent: Feb. 25, 1986

[54] TABLETS

[75] Inventors: Michael G. Lindley, Finchampstead; Steven Hathaway, Camberley, both of England

[73] Assignee: Tate & Lyle Public Limited Co., England

[21] Appl. No.: 553,867

[22] Filed: Nov. 21, 1983

Related U.S. Application Data

[63] Continuation of Ser. No. 369,493, Apr. 19, 1982, abandoned, which is a continuation-in-part of Ser. No. 203,450, Nov. 3, 1980, abandoned.

[30] Foreign Application Priority Data

Nov. 7, 1979 [GB] United Kingdom ............... 7938562
Jul. 3, 1980 [GB] United Kingdom ............... 8021825

[51] Int. Cl.$^4$ ............................................. A61K 47/00
[52] U.S. Cl. ..................... 514/777; 127/29; 127/30; 426/285; 426/658; 426/660
[58] Field of Search ............... 424/361, 363; 426/285, 426/658, 660; 127/29, 30; 514/777

[56] References Cited

U.S. PATENT DOCUMENTS

| | | | |
|---|---|---|---|
| 3,200,039 | 8/1965 | Thomson | 424/361 |
| 3,341,415 | 9/1967 | Scott | 424/361 |
| 3,424,842 | 1/1969 | Nurnberg | 424/361 |
| 3,446,899 | 5/1969 | Cavalli et al. | 424/361 |
| 3,619,292 | 11/1971 | Brouillard et al. | 424/363 |
| 3,627,583 | 12/1971 | Troy et al. | 424/361 |
| 3,639,169 | 2/1972 | Broeg et al. | 424/363 |
| 3,642,535 | 2/1972 | Graham et al. | 424/361 |
| 3,961,004 | 6/1976 | Nasir et al. | 424/361 |
| 4,007,052 | 2/1977 | Heinemann et al. | 424/361 |
| 4,013,775 | 3/1977 | Nelson et al. | 424/361 |

FOREIGN PATENT DOCUMENTS

| | | |
|---|---|---|
| 0001099 | 3/1979 | European Pat. Off. . |
| 1049800 | 7/1959 | Fed. Rep. of Germany . |
| 1429334 | 3/1976 | United Kingdom . |

OTHER PUBLICATIONS

Frank H. Stodola, et al., "The Preparation, Properties and Structure of the Disaccharide Leucrose", J. Amer. Chem. Soc., 78, 2514 (1956).

E. S. Sharpe, et al, "Formation of Isomaltulose in Enzymatic Dextran Synthesis", J. Org. Chem., 25, 1062 (1960).

*Primary Examiner*—Shep K. Rose
*Attorney, Agent, or Firm*—Ostrolenk, Faber, Gerb & Soffen

[57] ABSTRACT

Isomaltulose is of use for direct compression of tablets.

18 Claims, 1 Drawing Figure

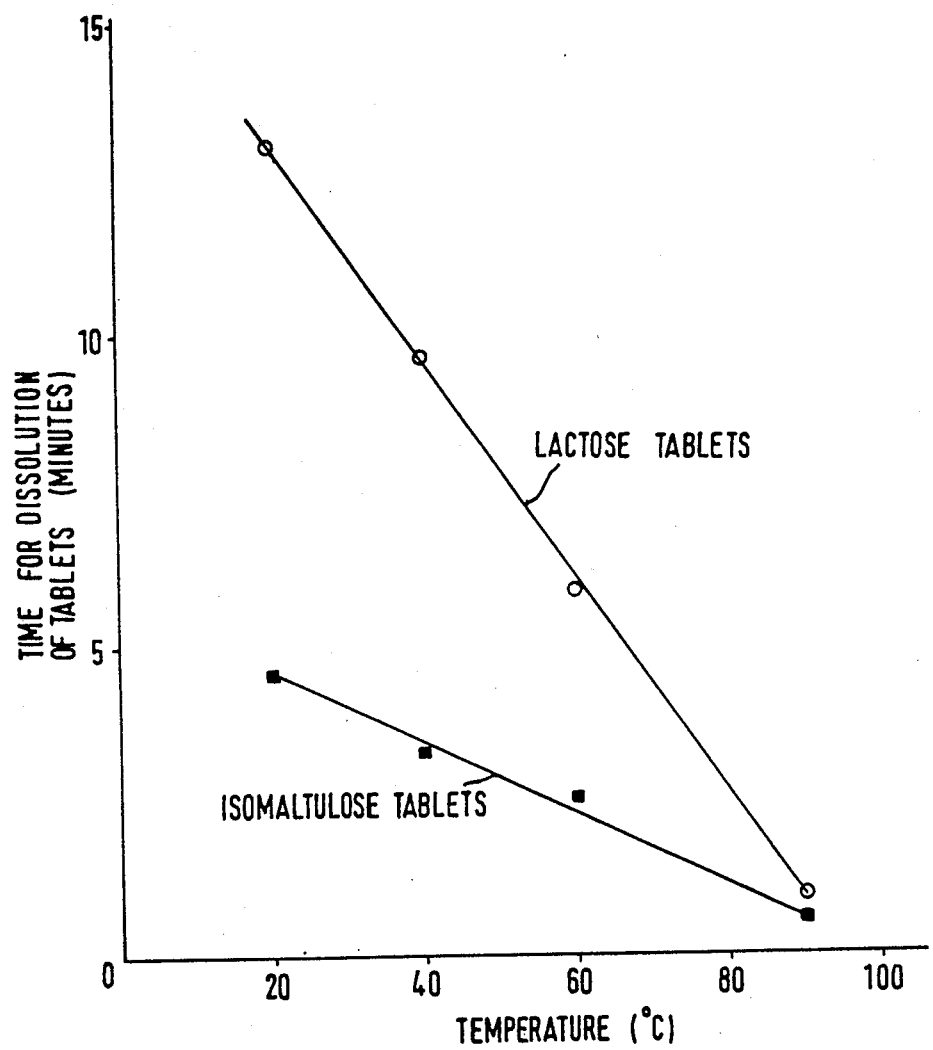

TABLETS

RELATED APPLICATION

This application is a continuation of Ser. No. 369,493 filed Apr. 19, 1982, which is a continuation-in-part of U.S. Ser. No. 203,450 filed Nov. 3, 1980 both now abandoned.

BACKGROUND TO THE INVENTION

The present invention relates to tablets, and in particular it relates to tablets which include a diluent material.

Tablets are conventionally made by moulding or compressing ingredients, and form a suitable means for delivery of an active ingredient, pharmaceutical or otherwise. There is also a large market for sweets in the form of tablets containing flavouring material as active ingredients.

In order to produce tablets, it is necessary to have a free-flowing material which has good self-binding properties and which will not stick to the moulding or compression equipment. Such properties are obtained by using diluents and one or more additives, for example binders and/or lubricants, and by controlled granulation of the ingredients. Some diluents of themselves possess binding and/or lubricating properties, but normally will require careful granulation.

Lactose is a commonly used diluent, having an acceptable taste. However, lactose alone has little adhesive property and normally requires the use of a binder. Moreover, moist granulation is usually needed, involving wetting of the ingredients to give a moist, coherent powder, then sieving, and controlled drying to give granules suitable for preparation of tabletting powders.

Sucrose, particularly sucrose of small particle size, is also a suitable diluent. Moist granulation is usual, unless one employs the specially formulated tabletting materials such as 'Di-Pac', a blend of maltodextrin and sucrose produced by Amstar Corporation of the United States of America using a microcrystallization process.

Other diluents are in use, for instance, starch, glucose, mannitol and sorbitol. Each of these materials offers its own advantages for certain uses, but as with lactose and sucrose, binders and/or lubricants along with controlled granulation are normally needed.

Direct compression, in which a simple mix of dry ingredients is compressed without further treatment, is a desirable alternative to procedures involving wet or dry granulation of an ingredient mixture. Nevertheless, as is explained, for example, in U.S. Pat. No. 3,627,583 to Troy and No. 3,639,169 to Broeg, the direct compression technique has been of limited applicability.

The principal problem with direct compression was the lack of a suitable vehicle. As is explained in the Troy and Broeg Patents, the vehicle has to meet various criteria, and the previously suggested materials such as lactose, dicalcium phosphate or microcrystalline cellulose all have failings.

A similar point is made in U.S. Pat. No. 3,961,004 to Nasir, where criticism is also given of the suggested use of mannitol or sorbitol as direct compression materials.

In turn, the U.S. patents to Troy and to Broeg each put forward a multi-component material which is manufactured by a special procedure to give a pre-prepared direct compression vehicle. Thus, U.S. Pat. No. 3,627,583 prepares certain sugar agglomerates using specific amounts of carefully defined ingredients and snowballing of the mixture to give agglomerates. It will be seen that this treatment to form agglomerates is tantamount to a granulation step before incorporation of the active ingredient. The prepared agglomerate is a direct compression vehicle, but the vehicle is a specially produced version of the sugar which is present.

In U.S. Pat. No. 3,693,169, a compaction aid is pre-prepared by compacting a dry mix to give a compact, nonfriable sheet and breaking up the sheet. In this way a direct compression vehicle is made for subsequent compression together with an active ingredient, but it is again the case that the vehicle is a specially produced version of the carrier material.

More generally, it is to be noted that direct compression vehicles have invariably comprised specially prepared versions of diluent or carrier compounds, the compounds usually being admixed with various additives or aids as part of the preparation of the direct compression vehicle.

OBJECTS OF THE INVENTION

It is an object of this invention to provide a direct compression vehicle which does not require special preparation or treatment before mixing with an active ingredient and subsequent tabletting.

It is a further object to provide a tabletting procedure which uses a non-granulated, non-compacted sugar as direct compression vehicle.

SUMMARY OF THE INVENTION

We have now found that isomaltulose, a disaccharide with limited previous uses, is especially suitable for use as a diluent material in tablets. Exceptionally, isomaltulose does not seem to require controlled granulation to give a tabletting powder. It is a simple matter to obtain tablets using direct compression of crystalline isomaltulose produced by conventional crystallization of isomaltulose solutions.

Isomaltulose is a reducing disaccharide which is sometimes known as palatinose. It has the structure

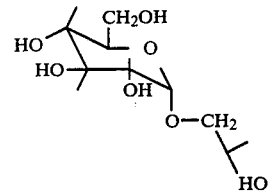

and is more systematically known as 6-O-(αglucopyranosyl)-D-fructofuranose.

Historically, isomaltulose was first mentioned in a 1952 article [J. Amer. Chem. Soc. 74, 3202 (1952)] as a by-product of a fermenting microorganims, *Leuconostoc mesenteroides*. Subsequent work publised in 1956 and 1960 [respectively, J. Amer. Chem. Soc. 78, 2514 (1956) and J. Org. Chem. 25, 1062 (1960)] confirmed the formation of isomaltulose as a by-product of dextran synthesis from sucrose by *L. mesenteroides*.

The bacterial conversion of sucrose to isomaltulose by *P. rubrum* was the subject of German Patentschrift No. 1,049,800 in the name of the Suddeutsche Zucker-Aktiengesellschaft. Other bacteria may be used to effect the conversion of sucrose to isomaltulose, and in their UK Patent Specifiation No. 1,429,334 (which corresponds to German Patentschrift No. 2,217,628), the same company mention that *Serratia plymuthica* is also suitable.

The UK Patent Specification No. 1,429,334 is itself directed the preparation of isomaltitol (α-D-glucopyranosyl-1,6-sorbitol) from isomaltulose by a catalytic hydrogenation. In practice, the hydrogenation gives a mixture that also contains α-D-glucopyranosyl-1,6-mannitol; this mixture is available as a low calorie sweetener under the trade name 'Palatinit'.

More recently, in their European Patent Specification No. 0001099, Bayer Aktiengesellschaft describe a process for continuous fermentation of micro-organisms, for example *Protaminobacter rubrum* or *Serratia plymuthica*, with simultaneous conversion of sucrose to isomaltulose. Again the isomaltulose is being prepared for hydrogenation to give the low calorie sweetener product.

Up until now, the hydrogenation of isomaltulose to a low calorie sweetener appears to have been the principal use for the compound.

In accordance with the present invention, we provide a tablet which contains isomaltulose as the or a diluent material.

Isomaltulose has a particular combination of physical and other properties which we have now discovered make it especially suitable for use as a diluent material in tablets. In particular, isomaltulose has better solubility in water than lactose, does not demand careful, controlled granulation and can be formed into tablets by direct compression with a lubricant.

Additionally, isomaltulose has a pleasant, not very sweet, reasonably bland taste and can allow other ingredients to exert a flavouring action. Isomaltulose can also contribute bulk, body, mouthfeel and other desired characteristics to tablets for human or animal consumption and to solutions for human or animal consumption prepared from tablets.

We have determined that isomaltulose has the properties shown in the following Table:

| Isomaltulose Properties | |
|---|---|
| solubility at 30° C., H$_2$O | 46 g/100 ml |
| viscosity at 25° C., 50% w/v, H$_2$O | 6 cp |
| $(\alpha)_D^{20}$ at 1% w/v | +97° |
| mp | 118-122° C. |
| mutarotation | nil |
| hydrolysis (90 h at 58° C. in 2M HCl) | 40% |
| reducing power | 58-62% of that of glucose |
| equilibrium relative humidity (at 80% and 22° C.) | 25-32% water |
| sweetness (relative to sucrose sweetness at 7% w/v in water). | 0.37 |

Apart from taking advantage of these determinable properties of isomaltulose, the present invention brings out unexpected beneficial properties of isomaltulose. Thus, tablets emloying isomaltulose as diluent often show less tendency to generate fines during handling than are generated during handling of comparable tablets using lactose as diluent. More generally, it was surprising to find that isomalutulose is a suitable replacement for lactose, particularly since other, more common saccharides do not lend themselves to direct tabletting. Isomaltulose seems to possess unusually good binding power when formed into tablets.

DESCRIPTION OF PREFERRED EMBODIMENTS

Isomaltulose can be used as diluent for various physiologically active ingredients. It can be used not only in pharmaceutical tablets, but also in other tablets containing other kinds of physiologically active ingredients, including flavouring materials. For example, isomaltulose can be used as diluent in sweetener tablets where the active ingredient is a high potency sweetening agent such as saccharin or the sweet protein thaumatin which is extracted from *Thaumatococcus daniellii* and which is commercially available as TALIN (Registered Trade Mark). Such tablets can be used for example to sweeten hot drinks.

In general terms, when proceeding in accordance with the present invention, isomaltulose can be used as a whole or partial replacement of other diluent materials in conventional formulations. Ideally the isomaltulose will be 100% pure, as may be obtained by bacterial conversion of sucrose using for example the processes described in German Patentschrift No. 1049800, UK Patent Specification No. 1492334 or European Patent Application No. 0001099. However, we find that acceptable results are obtained using once-crystallized material. Thus, in practice, the isomaltulose can be impure, containing up to 10, 20 or even higher percentage of other saccharides and accompanying matter.

In the specification of the Patent Application entitled "Production of Isomaltulose" which also claims a priority date of Nov. 7, 1979, (Ser. No. 201,462, filed Oct. 28, 1980 now U.S. Pat. No. 4,359,531) there is described a novel process using immobilized isomaltulose-forming enzyme systems to convert sucrose. The immediate product of this process is an isomaltulose solution also containing sucrose and by-products. Simple crystallization by conventional concentration and cooling procedures can be used to obtain crystals of 90% of higher content of isomaltulose. Such crystals are particularly suited to the manufacture of tablets.

The tablets of the invention can take any of the usual shapes, round, square or otherwise as determined by the equipment used. Suitably the isomaltulose will comprise up to 97% of the tablets of the invention, with 10 to 95% isomaltulose representing a currently preferred range. Apart from active ingredients, which will usually comprise 3 to 90% of the present tablets, and apart from other diluents, such as lactose, the tablets may further contain known tabletting additives, for instance to colour the tablets, to aid binding of the ingredients, to give effervescence, or to aid release of the tablets from a tabletting machine. The skilled man will be familiar with such additives (e.g. colouring agents, gum arabic, sodium stearate, starch) and further information is not needed from a sufficient description of the present invention. Tablets of the invention will usually weigh 5 mg to 5 g with 50 mg to 500 mg being preferred.

Preparation of the tablets of the invention can be performed using known techniques. In general, a mix of the isomaltulose and other ingredients is prepared, followed by moulding or compression. Various procedures are available to ensure proper intimate and thorough mixing of the ingredients and these procedures can be adopted as appropriate. In some instances, it may be necessary to modify the operating conditions so as to ensure that the temperature of the ingredients does not lead to melting of the isomaltulose or to oxidative reaction of the isomaltulose.

Unlike lactose and sucrose, isomaltulose crystals produced by ordinary crystallization procedures can give satisfactory tablets by direct compression after admixture with a lubricant and the intended active ingredient. Thus, in one embodiment of the invention, isomaltulose crystals prepared by crystallization from aqueous solution are dry mixed with a lubricant such as a fatty acid salt and with the active ingredient to be tabletted. Compression of the dry mix is then effected, giving tablets. Overall, this procedure offers advantages over the steps necessary to obtain tablets when using other, common diluents.

Isomaltulose should be acceptable for food and drug use. It has been used as an alternative for isomaltose in in vitro studies of isomaltose adsorption ("Some Recent Advances in Inborn Errors of Metabolism", Proceedings of Fourth Symposium of the Society for the Study of Inborn Errors of Metabolism held in Dublin, July, 1966, published as a book in 1968 by E. and S. Livingston, Ed Holt and Coffey, at page 106 in the paper by Holzen on Disaccharide Intolerances). As a result of these particular clinical studies, it appears that isomaltulose is readily hydrolyzed by an enzyme complex in the human intestine and that the constituent monosaccharides (fructose and glucose) are adsorbed, metabolized and otherwise behave as fructose and glucose derived from sucrose.

Moreover, preliminary studies indicate that although isomaltulose is metabolized by *Streptococcus mutans* (the bacterium thought to cause dental caries), little if any dental plaque is formed thereby. There are thus good reasons for believing isomaltulose to be non-cariogenic (that is, a compound which does not induce formation of dental caries).

The present invention is illustrated by the following non-limiting examples. In these Examples, the isomaltulose is crystalline material which is at least 90% pure and which has been prepared by the process of Example 1 in the specification of the said Patent Application entitled "Production of Isomaltulose". Isomaltulose produced by other methods can be used instead.

In Example 1 of the present specification reference is made to the accompanying drawing.

THE DRAWING

The accompanying drawing is a graph showing the solubility characteristics of tablets made using isomaltulose and of comparison tablets.

EXAMPLES

Example 1: Saccharin Tablets

To a mixture of 97 g isomaltulose and 3 g gum arabic was added sufficient 20% (w/v) gum arabic solution (12 to 13 g) until balls could be formed of the pasty mixture. After thorough mixing, the mixture was passed through a size 16 mesh sieve (1000 microns) and dried at 95° C. to give a tablet base composition.

The base composition was re-sieved and 42 g of it was intimately mixed with 10 g saccharin, 1 g gum arabic and 3 g sodium stearate, thereby giving a tablettable composition which was formed into about 1,000 tablets using a Manesty hand tabletting machine.

Each tablet was well-formed and retained its integrity.

We investigated the solubility characteristics of the tablets in comparison with lactose/saccharin tablets made in exactly the same way except that the isomaltulose was replaced by 96 g of lactose. For various temperatures in the range 20 to 90° C., the time taken for complete dissolution of the tablets was determined under standardized conditions.

The results of the solubility tests were plotted to provide the graphs shown in the accompanying figure: it will be seen that the isomaltulose-based tablets were consistently faster to dissolve than the lactose-based tablets. The faster solubility at the lower temperature is particularly noticeable.

Example 2: Vitamin C Tablets 90 parts (by weight, all parts being on this basis) of isomaltulose, were mixed with 10 parts of starch and the mixture granulated using 10% (w/v) starch paste. The resultant granules were dried at about 95° C. and screened with a size 16 sieve.

To 58 parts of the granules was added 10 parts of ascorbic acid (vitamin C), 11 part of starch and 1 part of stearic acid, thereby giving a tablettable composition which was formed into tablets. These tablets were of good shape and structure.

Example 3: Codeine Tablets

A mixture of 160 parts acetylsalicyclic acid, 160 parts phenacetin powder and 5 parts codeine phosphate was combined with 8 parts gum arabic, 10 parts starch and 35 parts isomaltulose in order to form granules. After drying at 95° C., the granules were then mixed with 10 parts starch and 12 parts talc to provide a tablettable composition which was then formed into tablets. Each tablet was of consistent shape and did not generate appreciable fines during handling. Dissolution in water was fast.

EXAMPLE 4

Further comparisons with lactose were carried out during the preparation of saccharin tablets.

(i) Direct compression 50 g isomaltulose, 4 g gum arabic, 1 g magnesium stearate and 13 g saccharin were dry mixed, giving a flowable tabletting powder. Tablets were formed by direct compression of the powder. No problems with sticking were encountered during compression, and the resultant tablets were hard, cohesive, and yet readily soluble.

In contrast, it was not possible to produce coherent tablets using either 50 g lactose or 50 g icing sugar in place of the isomaltulose.

(ii) Simplified direct compression

A tabletting powder based on isomaltulose was produced in the same way as in Example 4(i) except that the binder (gum arabic) was omitted. Despite the omission of the binder, tablets could still be successfully made by direct compression.

Tablets could not be made using lactose or icing sugar in place of the isomaltulose.

Example 5: Mint Sweet

Confectionery in the form of mint-flavoured sweet tablets was made using the following ingredients:

| Ingredient | Amount (parts by weight) |
| --- | --- |
| Sucrose | 46 |
| Isomaltulose | 46 |
| 42DE syrup | 3 |

| Ingredient | Amount (parts by weight) |
|---|---|
| Oil of peppermint | 3.2 |
| Water | 1.2 |
| Magnesium stearate | 0.25 |

The sucrose, isomaltulose, syrup and water were mixed together, extruded in conventional manner and dried at 60° C. to give granules.

The granules were sieved using a size 30 mesh (0.551 mm) and the oil of peppermint added along with the magnesium stearate. Tabletting in the usual way then gave firm, coherent tablets which dissolved in the mouth, releasing a pleasant peppermint flavour.

Example 6: Aspirin Tablets for Children

The following formulation was used to evaluate six carriers:

| Aspirin (20 mesh) | 40.5 g |
|---|---|
| Excipient** | 50.0 g |
| Starch* | 5.0 g |
| Magnesium stearate | 4.0 g |
| Flavour qs | |

*Laing National "Crystal Gum S" tabletting starch.
**Excipients:
(i) Isomaltulose - crystallized material
(ii) Dipac - Amstar
(iii) Emdex - Edward Mendell Co
(iv) Lactose - BDH Drug Houses
(v) Icing Sugar - T & L Refineries
(vi) Anhydrous dextrose - BDH Procedure:

(a) The aspirin was mixed with the carrier under test, taking care to avoid moisture pick-up. The flavour was added to the starch with thorough mixing. The magnesium stearate was then added to the starch and this combination blended, with agitation, with the aspirin-carrier mix.

(b) The blend was then evaluated for flowability by timing the flow through a ⅜ inch orifice funnel-shaped flow meter, with no vibration.

The time for 100 g of the tablet mix to flow through the 3/8 inch orifice funnel was measured.

| Carrier | Time (seconds) |
|---|---|
| Isomaltulose | 38 |
| Dipac | 34 |
| Emdex | 42 |
| Lactose | No flow |
| Icing sugar | No flow |
| Anhydrous Dextrose | No flow |

"No flow" indicates that the mix was unable to flow completely through the funnel without agitation.

Clearly isomaltulose is comparable with the specially prepared products Dipac and Emdex, and better than the lactose, icing sugar or anydrous dextrose.

(c) Tablets were made using a ¼ inch flat face punch with the following results:

| (i) Isomaltulose: | Tablets successfully made Released from die easily Good shiny appearance Good integrity |
|---|---|
| (ii) Dipac: | As (i) |
| (iii) Emdex: | As (i) |
| (iv) Lactose: | Irregular flow gave problems of tablet integrity Usually did not form cohesive tablets. Tablet machine prone to sticking. |
| (v) Icing sugar: | As (iv) |
| (vi) Anhydrous dextrose | As (iv) |

Again it is clear that isomaltulose is comparable with the Dipac and Emdex, and superior to the other carriers.

(d) The tablet weights were:

| Isomaltulose | 151 mg |
|---|---|
| Dipac | 155 mg |
| Emdex | 155 mg |

Evaluation of the weight of the other tablets was not possible in view of the manufacturing difficulties, see (c).

(e) Tablet hardness was then assessed. For an objective test, the tablets were vibrated in a container for 1 hour. The % weight loss was recorded and was as follows:

| Isomaltulose | 3.2% |
|---|---|
| Dipac | 0.5% |
| Emdex | 0.5% |

Example 7: Ascorbic Acid Tablets:

Using the same procedure as in Example 6, the following formulation was employed:

| Ascorbic Acid | 55.0 g |
|---|---|
| Excipient | 63.5 g |
| Magnesium Stearate | 1.0 g |

Once again, isomaltulose performed well on flowability, but not so well on tablet hardness.

| Flowability | 100 g through ⅜" orifice, no agitation |
|---|---|
| Isomaltulose | 43 seconds |
| Dipac | 39 seconds |
| Emdex | 46 seconds |
| Dextrose, Lactose, Sucrose | Agitation required |

Weight loss on vibration for 1 hour.

| Isomaltulose | 1.8% |
|---|---|
| Dipac | 0.4% |
| Emdex | 0.3% |

Again, tablets with isomaltulose were shiny, hard and had good appearance. They were not as hard as with the specially formulated carriers but in general the isomaltulose was clearly superior to the dextrose, lactose and sucrose.

We claim:

1. In the method of making tablets consisting essentially of tableting by direct compression a dry mix containing 3 to 90% of at least one active ingredient, the improvement comprising employing as a direct tableting aid, 10–95% crystallized, non-granulated and non-compacted isomaltulose.

2. A directly compressed binder-free non-granulated tablet consisting essentially of 10 to 95% non-compacted prior to tableting crystalline isomaltulose having the structure

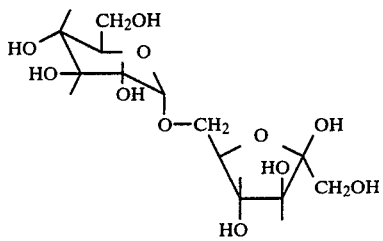

and 3–90% of at least one active ingredient, admixed together with a lubricant produced by the process of claim 1.

3. The method of claim 1, wherein the isomaltulose is isomaltulose directly obtained by crystallization from aqueous solution.

4. The method of claim 1, wherein said tablettable powder also contains a lubricant.

5. The method of claim 1, wherein said isomaltulose contains up to 20% impurities introduced during the preparation of said isomaltulose from sucrose.

6. The method of claim 5, wherein said isomaltulose is at least 90% pure.

7. The method of claim 1, wherein said active ingredient is a pharmaceutically active ingredient.

8. The method of claim 1, wherein said active ingredient is a sweetener.

9. The method of claim 1, wherein said tablettable powder does not contain a binder.

10. A tablet consisting essentially of a directly compressed dry mix containing 10 to 95% crystallized non-granulated and non-compacted isomaltulose and 3–90% of at least one active ingredient produced by the process of claim 1.

11. The tablet of claim 10 consisting essentially of said isomaltulose, said active ingredient and a lubricant.

12. The tablet of claim 11 wherein said isomaltulose contains up to 20% impurities.

13. The tablet of claim 11 wherein said active ingredient is a pharmaceutically active ingredient.

14. The tablet of claim 11 wherein said active ingredient is a sweetener.

15. The tablet of claim 2 wherein said active ingredient is a pharmaceutically active ingredient.

16. The tablet of claim 2 wherein said active ingredient is a sweetener.

17. The method of claim 1 which consists essentially of tableting by direct compression a dry mix containing 10 to 95% of non-granulated and non-compacted crystalline isomaltulose of the structure

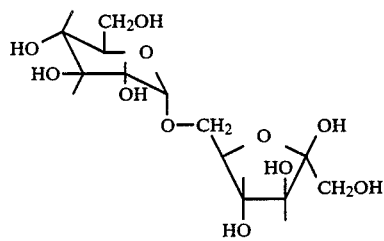

and containing up to 20% impurities introduced during the preparation of said isomaltulose from sucrose and 3 to 90% of at least one active ingredient, admixed together with a lubricant in the absence of a binder.

18. The tablet of claim 10 wherein said isomaltulose, prior to compaction, was non-granulated and non-compacted.

* * * * *